(12) United States Patent
Labreche

(10) Patent No.: US 10,539,541 B2
(45) Date of Patent: Jan. 21, 2020

(54) METHOD AND DEVICE FOR CHARACTERISING AN ANALYTE

(71) Applicant: ALPHA M.O.S, Toulouse (FR)

(72) Inventor: Saïd Labreche, Buzet-sur-Tarn (FR)

(73) Assignee: ALPHA M.O.S., Toulouse (FR)

( * ) Notice: Subject to any disclaimer, the term of this patent is extended or adjusted under 35 U.S.C. 154(b) by 231 days.

(21) Appl. No.: 15/661,633

(22) Filed: Jul. 27, 2017

(65) Prior Publication Data
US 2018/0031530 A1 Feb. 1, 2018

(30) Foreign Application Priority Data

Jul. 28, 2016 (EP) ..................................... 16305986

(51) Int. Cl.
| | |
|---|---|
| *G06F 11/30* | (2006.01) |
| *G01N 30/86* | (2006.01) |
| *G06K 9/00* | (2006.01) |
| *G01N 25/00* | (2006.01) |
| *G01N 27/12* | (2006.01) |
| *G01N 30/02* | (2006.01) |

(52) U.S. Cl.
CPC ......... *G01N 30/8631* (2013.01); *G01N 25/00* (2013.01); *G01N 27/125* (2013.01); *G01N 30/8634* (2013.01); *G01N 30/8644* (2013.01); *G06K 9/00557* (2013.01); *G01N 2030/025* (2013.01)

(58) Field of Classification Search
CPC ................................................ G01N 30/8631
See application file for complete search history.

(56) References Cited

U.S. PATENT DOCUMENTS

2008/0046195 A1* 2/2008 Labreche ............. G06K 9/6253
702/30

FOREIGN PATENT DOCUMENTS

| EP | 1598666 A1 | 11/2005 |
|---|---|---|
| EP | 1845479 A | 10/2007 |

(Continued)

OTHER PUBLICATIONS

European Search Report for 16305986.8 dated Feb. 7, 2017.

*Primary Examiner* — Phuong Huynh
(74) *Attorney, Agent, or Firm* — Meagher Emanuel Laks Goldberg & Liao, LLP

(57) ABSTRACT

A method and apparatus are provided for characterizing a product sample for example in comparison to a reference sample using a sensor such as a gas chromatograph or a MOS sensor. This characterization may comprise an indication of whether or not the product sample conforms to a quality criterion. The comparison of the sensor output measurements for the product sample is compared to maximum and minimum value curves, which may be derived from measurements of the reference sample, whereby adjacent samples outside the envelope defined by these maximum and minimum values are grouped together. A dissimilarity index may be determined for the anomalous values as a whole, or on a per group basis. The groups may be classified depending on the shape they describe, in particular the presence, or not, of peaks, and correspondingly the shape of the corresponding part of the envelope. These determinations may then be used as the basis of the conformity indication, and also the basis for attempting to identify the cause of any anomalies, in particular the identification of foreign components.

13 Claims, 10 Drawing Sheets

(56) References Cited

FOREIGN PATENT DOCUMENTS

| | | |
|---|---|---|
| EP | 2718705 A1 | 12/2012 |
| JP | 2006170647 A | 6/2006 |
| WO | 020086491 A1 | 10/2002 |
| WO | 2012168444 A1 | 12/2012 |

* cited by examiner

METHOD AND DEVICE FOR CHARACTERISING AN ANALYTE

FIELD OF THE INVENTION

The present invention relates to product quality control with regard to the comparison between the product and its standard reference.

BACKGROUND ART

Detection of chemical components designates the identification of the type and/or quantity of a chemical component. In the general field of chemical detection, an analyte designates a substance or component of particular interest for a chemical measurement. A transducer is an element that converts the information from a sensor into a physical signal (for example electrical intensity) representative of the detection of substance or components by the sensor. The sensitivity represents the ability of a sensor to detect even a small quantity of a component. The selectivity designates the ability to precisely determine the component that has been detected by a sensor.

A large number of biochemical sensors exist. For example, gas chromatography consists in passing gas components in a column. For a definite composition of a static phase in the column, each type of component is characterized by a specific duration for crossing the column, which is called retention time. In usual gas chromatography systems, a detector is placed at the end of the column, which outputs at any time a value representative of the quantity of components that leaves the column. A component that is present with a large concentration in a fluid processed in a gas chromatograph therefore generates a peak of intensity around the retention time characterizing the component. The analysis of gas chromatography peaks, and comparison with reference values for a set of analytes is a widely used method of determination of the type and quantity of components present in a fluid.

However, the selectivity of a gas chromatography sensor may be limited if several components have comparable retention times, or if the time resolution of the sensor at the end of the column is not high enough to disambiguate the peaks generated by two different analytes.

CMOS gas sensors, for example metal oxide gas sensors form another family of biochemical sensors for the detection of components in a gas. A metal oxide gas sensor modifies the sensitivity of an electrical component according to the concentration of some components in a gas, and parameters specific to the sensor, such as the chemical composition of the sensing layer, and the temperature at the surface of the layer. Some metal oxide sensors are designed in terms of surface composition and temperature to precisely detect a single analyte. On the other hand, some metal oxide sensors are designed to generate measurement at various temperatures, the change of sensitivity due to each analyte varying with the temperature of the surface of the sensor. However, due to the large number of possible analytes and the possibility that many analytes modify the sensitivity of the sensor at the same temperature, the selectivity of such a sensor to a large number of analytes remains low. Such drawback may be mitigated by using 2D arrays of CMOS sensors, each sensor in an array being sensitive to different analytes in a gas. Also, 3D stacks of CMOS sensors can be used to increase selectivity of the sensor arrangement, such as those disclosed in the European patent application co-assigned to the applicant of this application which is published under no EP2718705.

The determination of analytes is generally based on a comparison of actual measurements with reference values obtained from a library. For example, in gas chromatography an analyte can be identified by comparing the retention time of a peak to a set of theoretical retention times for different analytes in the same gas chromatography column. However, the determination of the type of an analyte requires that a theoretical value already exists from a reliable source for this analyte. Due to the large number of possible analytes, it is therefore desirable to use theoretical data from a number of sources as large as possible.

In gas chromatography, the Kovats index is a generalization of the retention time of a compound for a type of column, a type of column being determined by the stationary phase of the column. The values of retention times for each peak can be converted, according to parameters such as the length of the columns, the temperature, etc to a Kovats index which only depends of a type of column, therefore allowing comparison between different columns having the same stationary phase, and the collaborative creation of large databases.

While it is possible to imagine a large database containing reference data for each individual possible analyte, such an approach assumes that the sample analyte to be characterized corresponds to a simple individual reference analyte. In many real world scenarios, the analyte will contain complex mixtures of components, each of which may correspond to a greater or lesser extent to a particular reference analyte, and some of which may be unknown in the database altogether.

One known use of systems of this kind is to determine whether an analyte meets, or does not meet, certain quality criteria. On the basis of the foregoing techniques, the conventional approach is to perform a statistical comparison of measurements performed for a sample analyte with a reference dataset.

This statistical comparison may be carried out by means of multivariate analysis techniques such as k-NN (k-Nearest Neighbour), CA (Cluster Analysis), DFA (Discriminant Function Analysis), PCA (Principal Component Analysis), PCR (Principal Component Regression) Multiple Linear Regression (MLR), hierarchical cluster analysis (HCA) and the like. A problem of this approach is that these comparisons are not able to distinguish effectively between characteristic variations which are suggestive of a quality issue, and other, random sample variations which are of little interest. As such, these prior art techniques tend to either assess all samples as acceptable, or if very demanding criteria are set, assessing many analytes as not matching although the variations detected do not correspond to quality issues.

EP1845479 represents a partial solution to certain of these problems. Nevertheless, it is desirable to provide a more rapid and effective mechanism for determining on the basis of the results of such a chemical analysis whether a new product sample demonstrates deviations from a reference sample for that product, and whether in view of any such deviations the product can still be considered to meet quality criteria. In particular, it is desirable to provide a mechanism able to reliably detect a larger proportion of samples not meeting the quality criteria without increasing the incidence of rejecting acceptable samples.

SUMMARY OF THE INVENTION

In accordance with the invention in a first aspect, there is provided a method of for characterizing an analyte of a specified category, comprising the steps of:
- receiving a first series of measurements of a physical parameter from a sensor,
- comparing each said measurement in said first series with a corresponding minimum value in a second series defined for said specified category and a corresponding maximum value in a third series defined for said specified category,
- grouping any adjacent said measurements where each said measurement in said group exceeds said corresponding maximum value or where each said measurement in said group each falls below said corresponding minimum value, and
- flagging each said group as anomalous.

In accordance with a development of the first aspect the characterization comprises an indication of whether the analyte meets a quality criterion, and where the method comprises a further step of determining whether the groups reflect a departure from the quality criterion.

In accordance with a development of the first aspect the method comprises the additional step of defining the second series and the third series on the basis of one or more sets of measurements performed for one or more samples known to be representative of a particular analyte.

In accordance with a development of the first aspect the method comprises an additional step of advancing or delaying the first series with respect to the second and third series so as to obtain the best possible alignment.

In accordance with a development of the first aspect the method comprises an additional step such that where any measurement exceeds the corresponding maximum value a dissimilarity index is calculated for that respective measurement exceeding said corresponding maximum value, said dissimilarity index reflecting the degree by which said corresponding maximum value is exceeded, and where any measurement falls below the corresponding minimum value the dissimilarity index is calculated for that respective measurement falling below said corresponding minimum value, said dissimilarity index reflecting the degree by which said measurement falls below said corresponding minimum value.

In accordance with a development of the first aspect the method comprises an additional step of classifying each group into a respective classification selected from a predefined set of classifications, where each classification in the predefined set of classifications describes the form of the measurements comprising the respective group and the form of the corresponding values of the second series, the third series, or a fourth series representing the average values across the sets of measurements where more than one set of measurements of the representative analyte are performed.

In accordance with a development of the first aspect at least one of the classifications corresponds to a situation where:
- a respective group defines an extremum and the corresponding values in the second series, third series, or fourth series also define an extremum; or
- a respective group defines an extremum and the corresponding values in second series, third series, or the fourth series do not define an extremum; or
- a respective group does not define an extremum and the corresponding values in the second series, the third series, or the fourth series do define an extremum; or
- neither a respective group nor the corresponding values in the second series, the third series, or the fourth series define an extremum, and the values of the measurements in a respective group exceed the corresponding values in the second series; or
- neither a respective group nor the corresponding values in the second series, the third series, or the fourth series define an extremum, and the values of the measurements in a respective group fall below the corresponding values in said third series.

In accordance with a development of the first aspect the method comprises the further steps of: comparing the measurements in one or more groups to a set of additional reference datasets;
identifying the reference data set in the set of additional reference sets corresponding most closely to the measurements in the group; and
associating the analyte with characteristics of the corresponding reference data set.

In accordance with a development of the first aspect the steps of comparing the measurements in each group to a set of additional reference datasets, and identifying the reference data set corresponding most closely to the measurements are performed with regard to the classifications.

In accordance with a development of the first aspect the sensor is any sensor producing a value evolving over time when exposed to an analyte, and wherein the first series of measurements varying monotonically within a range of values, corresponds to a series of measurements obtained over a measurement period.

In accordance with a development of the first aspect the sensor is a MOS sensor or a Gas Chromatograph.

In accordance with a second aspect, there is provided an apparatus for characterizing an analyte of a specified category, adapted to receive a first series of measurements of a physical parameter from a sensor, compare each measurement in the first series with a corresponding minimum value in a second series defined for the specified category and a corresponding maximum value in a third series defined for the specified category, group any adjacent the measurements where each measurement in the group exceeds the corresponding maximum value or where each measurement in the group each falls below the corresponding minimum value, and to flag the groups as anomalous.

In accordance with a third aspect, there is provided an apparatus adapted to implement the first aspect.

In accordance with a fourth aspect, there is provided a computer program adapted to implement the first aspect.

BRIEF DESCRIPTION OF THE DRAWINGS

The invention will be better understood and its various features and advantages will emerge from the following description of a number of exemplary embodiments and its appended figures in which.

DETAILED DESCRIPTION OF THE INVENTION

When measuring instruments like a gas chromatogram (GC) or a gas sensor (GS) are used to analyze a product, a set of time dependent data are generated. Some parts of the chromatogram are associated to peaks. Each peak generally corresponds to one of more analytes forming the analyzed complex product. For GS, one might consider three parts to the data, comprising an ascending part, a maximum, and a descending part.

Only selected measurements from the complete set of values provided are generally taken into account to build libraries that will be used for data treatment: For example, the surface of some peaks for GC or the maximum of the sensor response for GS. In this context, a library may be a data table, where each line is associated to an analyzed product and each column is associated to a variable. For GS, each variable represents the optimum of sensor gas sensitivity. For GC, each variable represents an interval of retention times containing at least one peak observed at least on one analyzed product.

In this specification, the invention will be described by way of examples relative to GC and CMOS sensors. However the invention is not restricted to these sensors, and can be applied to any sensors for which a change of the value of a first physical parameter implies changes of a value of a second physical parameter representative of at least the concentration of an analyte.

Figure 1:
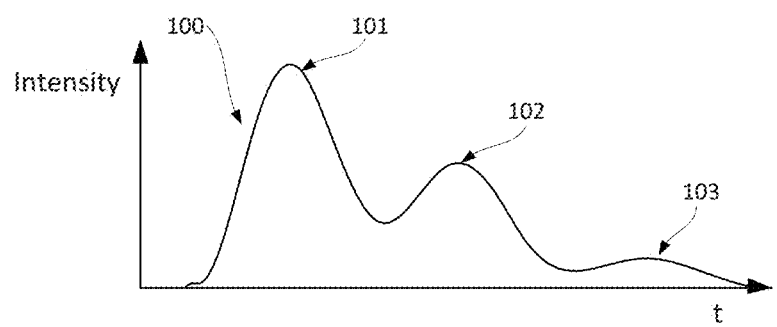
FIG. 1 represents an exemplary output of measurements for a sensor compatible with embodiments of the present invention.

FIG. 1 represents an exemplary output of measurements for a sensor compatible with embodiments of the present invention.

FIG. 1 may correspond to an output of measurement of a gas chromatography columns Curve 100 represents the output of sensing procedures using a Gas Chromatography sensors on a gas compound, which contains a single analyte. A retention time represented on horizontal axis, an intensity of measurement representative of the amount of particles that leaves the column at the retention time, is represented on the vertical axis. Peaks of intensity 101, 102, 103 clearly appear at successive retention times that characterize the analytes on the column. In this example, the retention times of peaks 101, 102, 103 are different. The analysis of the retention time of a peak in a GC column, or the Kovats index of a peak in a GC column type, is an indication of the type of analytes, while the intensity of the peak is an indication of a relative amount of the corresponding analyte. The Kovats index being a normalized measure, large database of reference Kovats index exist, for example the NIST database. Comparing a measured Kovats index to reference index in a database permits to identify a candidate analyte. However, a plurality of different analytes may have very similar retention times. It may therefore be difficult, observing a peak, to identify one peak among a plurality.

A similar output may be output as the result of measurement by a Metal Oxide Sensor.

MOS gas sensors are generally made of a heated plate of metal oxide sensor material. According to parameters that notably include the structure of the sensor, the material of the plate and the operating temperature, the sensor absorbs analytes that generate variations of the sensitivity of the plate. The measurement of the sensitivity of the plate allows the detection of analytes. Some MOS gas sensors are very selective and react to precise analytes. Other types of MOS sensors are able to detect a plurality of analytes, the variations of the sensitivity in contact to an analyte varying according to physical parameters such as the temperature of the plate, the wavelength of an UV pulse illuminating the plate, and the intensity of a current that polarizes the sensor.

Databases are typically constructed by capturing measurements with sensors for known analytes. They can be public databases like the NIST database for Gas Chromatography, or private databases built internally in an entity. They may contain reference values related to a particular sensor, for example retention times for a GC column from a manufacturer, or normalized values that apply to a sensor type, for example reference Kovats indexes for analytes and a GC column type.

Figure 2:
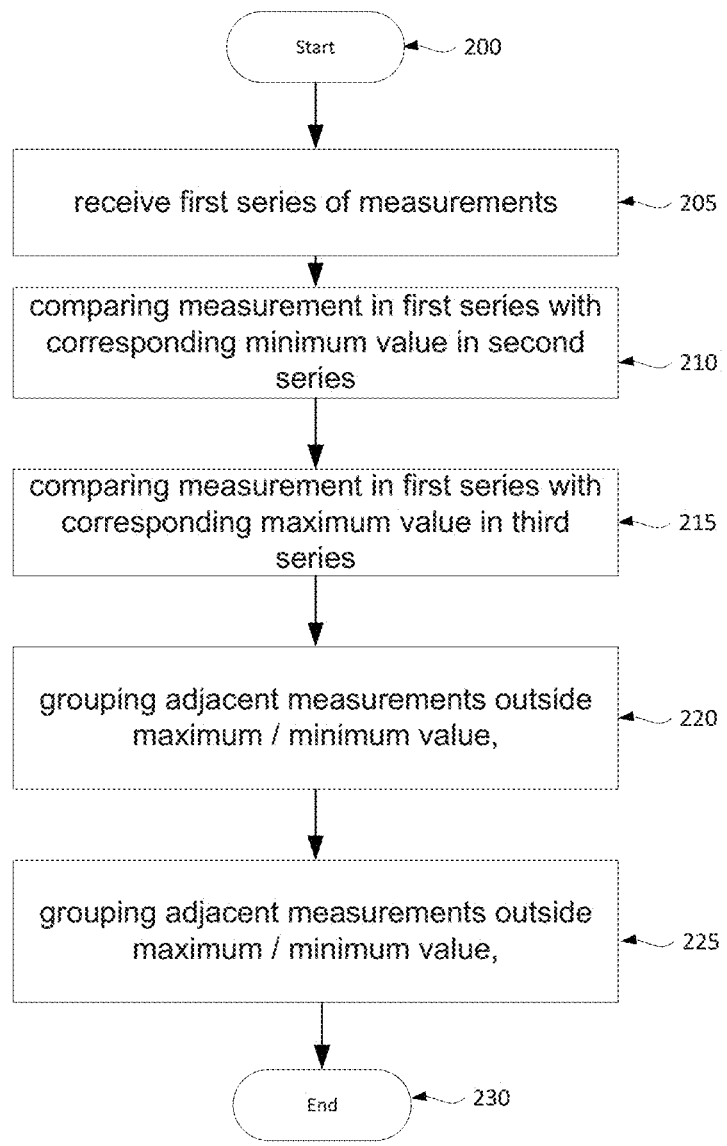
FIG. 2 shows a method according to an embodiment.

FIG. 2 shows a method according to an embodiment.

As shown in FIG. 2, there is provided a method of for characterizing an analyte of a specified category.

The characterizing referred to here may constitute a determination that the analyte meets, or does not meet, certain quality criteria.

Depending on the sensor used, embodiments may be directed to characterizing an analyte in a fluid. The term fluid as used throughout the present description should be understood in its broadest sense, that is, any medium which is able to flow in the temperature and pressure ranges in which measurements may be taken. Accordingly, fluids may include liquids, gases, plasmas, viscous solids or masses of dust or powder. Fluids may also include a combination of such substances, which may be of similar or homogenous types, such as emulsions, aerosols, particles of solid or liquid dispersed in a gaseous carrier or otherwise. This may include a fluid comprising only one, or a plurality of different molecules, some or all of which may correspond to the sample to be characterised, while others may be inert or otherwise merely serve as carriers, and not to be characterised.

It should also be born in mind that the phase of matter of the sample is of significance in that it is in this phase that the sample is expected to react with the sensor. It is entirely possible that in parts of the system away from the gas sensor, the sample may exist in another form.

As shown in FIG. 2, the method starts at step 200 before proceeding to step 205 at which a first series of measurements of a physical parameter is received from a sensor.

In particular, the sensor may be any sensor producing a value evolving over time when exposed to an analyte, and the first series of measurements may thus correspond to a series of measurements obtained over a measurement period.

By way of example, the sensor may be a MOS sensor or a Gas Chromatograph as described above.

The first series of measurements may take the form of a series of sample values. These may represent the output of the sensor at predetermined intervals, or the average output over a predetermined interval, or otherwise. The predetermined intervals may be of fixed and equal duration, or may vary from one sample to the next in accordance with a predefined program, or may be dynamically determined for example as a function of the detected rate of change of output values. Where the output of the sensor is a continuous analogue signal, at some point the signal may be sampled to obtain the first series of measurements.

Figure 3:
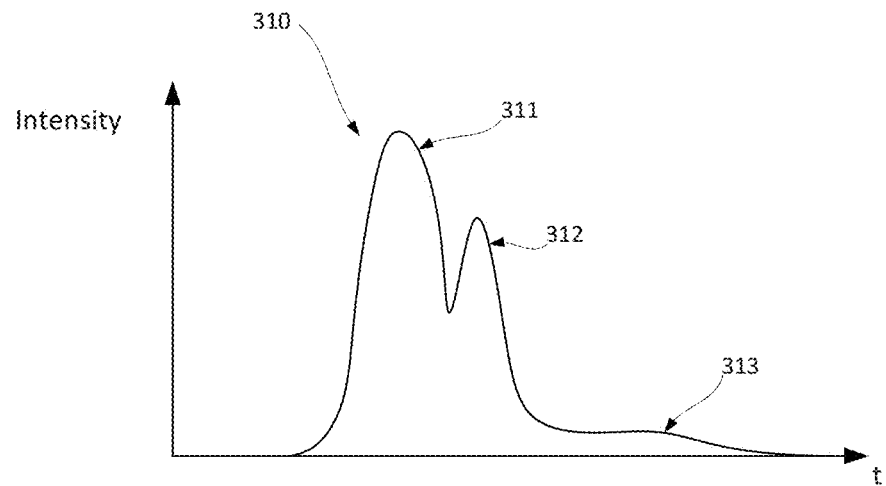
FIG. 3 shows a representation of an exemplary first series of measurements in accordance with the embodiment of FIG. 2.

FIG. 3 shows a representation of an exemplary first series of measurements in accordance with the embodiment of FIG. 2.

FIG. 3 follows the same layout as FIG. 1 as described above, with Intensity plotted on the vertical axis and time on the horizontal axis. For the sake of the present example, it may be assumed that the curve 310 of FIG. 3 is the result of measurement for a sample of the same type as the curve shown in FIG. 1. Accordingly, it might be expected that the curves of FIGS. 1 and 3 should be identical, however for the reasons discussed above, in practice test samples are rarely an exact match for the corresponding reference sample, and it is an objective of certain embodiments to overcome or characterize these divergences. Accordingly, as shown the curve 310 comprises a first peak 311, a second peak 312 and a third peak 313. It may further be noted that the curves of FIGS. 1 and 3 are represented as continuous curves, whereas in accordance with step 205 as described above, they in fact comprise a series of discrete values, or measurements. For the sake of the present example it is assumed that the number of measurements is sufficiently large that the curve appears to be smooth and continuous. In other cases this need not be the case.

As noted with respect to step 205, the set of measurements 310 corresponds to a specified category. The category of the set of measurements may be defined according to a classification of any degree of granularity, as may be suitable for the context of the invention.

Preferably, the specified category will correspond as closely as possible to the type of sample to be characterised. The specified category may be selected on the basis of any available information about the type of sample being characterised. This may involve user input in order to provide any available information about the sample—for example, the user might specify that the sample was a particular product, or type of product, which may then provide a basis for selecting the specified category. Alternatively, the system may communicate with other devices to obtain relevant information—for example, a connected refrigerator may be able to provide information about its contents, or product packaging may have bar codes, RFID tags or other identifiers that can be used to retrieve additional information supporting optimal selection of the specified category. Different categories may in some cases be applicable depending on readings of ambient conditions such as temperature, pressure and humidity.

Categories may be defined in a hierarchical structure, for example with each level in the hierarchy corresponding to different sub-categories of the type of sample under study. For example if the sample category is "Coffees", a specified category may be provided for various different sub-categories (species, origin, condition, taste profile, quality, etc.).

In certain embodiments, in particular where the characterizing to be performed constitutes a determination that the analyte meets, or does not meet, certain quality criteria, the category may simply designate a reference sample for the product itself, such that the characterisation can then comprise an indication of whether or not the analyte matches, or does not match, the reference sample for the sample product, within certain tolerances as discussed further hereafter.

Figure 4:
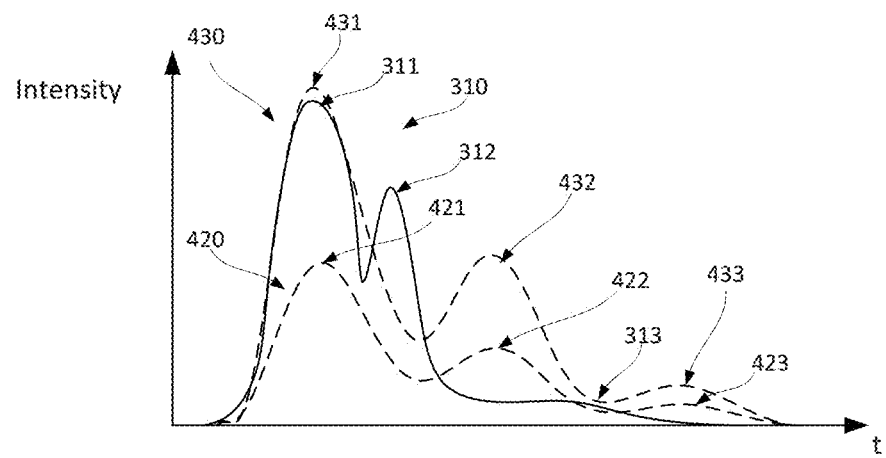
FIG. 4 shows a representation of an exemplary second and third series of values in accordance with the embodiment of FIG. 2.

FIG. 4 shows a representation of an exemplary second and third series of values in accordance with the embodiment of FIG. 2.

FIG. 4 follows the same layout as FIG. 1 as described above, with Intensity plotted on the vertical axis and time on the horizontal axis. The first series of measurements 310 as shown in FIG. 3 is plotted identically in FIG. 4. Additionally the curve corresponding to the second series of minimum values 420 and the curve corresponding to the third series of maximum values 430 is shown. It may be noted that the forms of curves 420 and 430 correspond to that of curve 100 as described with reference to FIG. 1. Specifically, the curve 420 has peaks 421, 422 and 423 corresponding to peaks 101, 102 and 103, the curve 430 has peaks 431, 432 and 433 corresponding to peaks 101, 102 and 103. This reflects the notion that the maximum and minimum values are defined by the accumulation of a number of sets of measurements performed for one or more representative samples of the selected category, where the curve of FIG. 1 is taken to represent one such set of measurements performed for a representative sample of the selected category.

It may be observed that as shown in FIG. 4, the alignment on the time axis of the first curve 310 with the second and third curves 420, 430 is poor. In certain implementations this may be a matter of calibration or otherwise represent a variation which does not correspond to an underlying difference between the samples. As such, there may be provided an optional step of advancing or delaying the first series with respect to the second and third series so as to obtain the best possible alignment.

Figure 5:
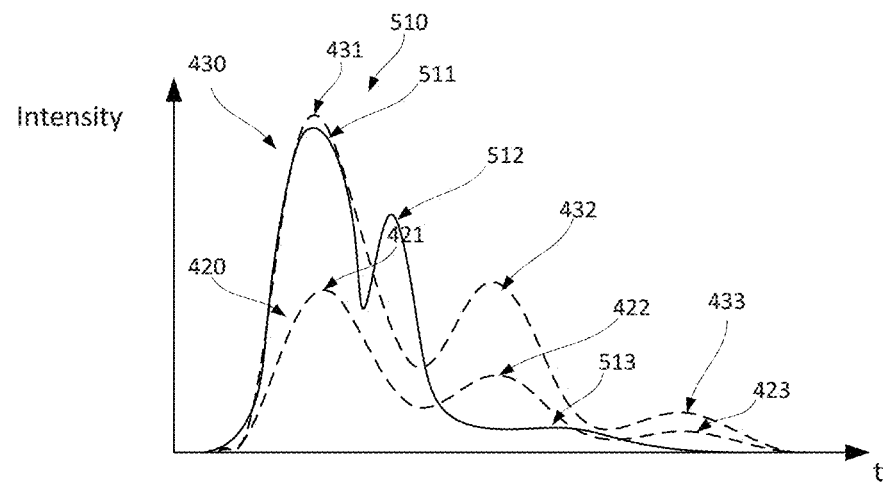
FIG. 5 shows a representation of an exemplary second and third series of values in accordance with the embodiment of FIG. 2 with the first series subjected to realignment in the horizontal axis.

FIG. 5 shows a representation of an exemplary second and third series of values in accordance with the embodiment of FIG. 2 with the first series subjected to realignment in the horizontal axis.

FIG. 5 follows the same layout as FIG. 1 as described above, with Intensity plotted on the vertical axis and time on the horizontal axis. The first series of measurements 510 as shown in FIG. 5 is plotted similarly to the curve 310 of FIGS. 3 and 4, however it has been realigned on the horizontal axis so that the peak 511 aligns with the peaks 431 and 421, and the peak 512 aligns with the peaks 432 and 422.

Whether or not the first series of measurements is re-aligned as described with reference to FIG. 5, the method next proceeds to step 210, at which each measurement in the first series is compared with a corresponding minimum value in the second series defined for the specified category.

Figure 7:
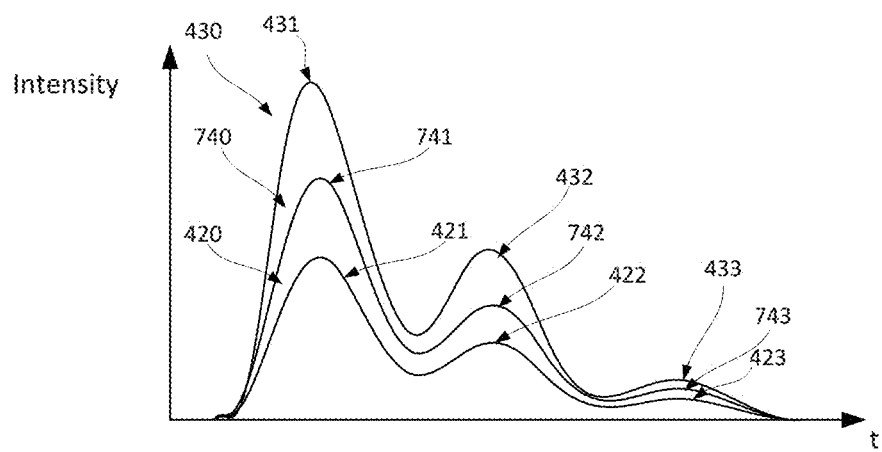
FIG. 7 shows a representation of an exemplary second and third series of values in accordance with the embodiment of FIG. 2 defined with reference to a fourth series.

The second, third and as applicable fourth series may be obtained from the measurement of a series of samples as described further with respect to FIG. 7. Where n sets of measurements of reference samples are available, the $i^{th}$ sample may be associated with a vector S(i,) of m measures. S (i,j), the generic term of the vector with j=1 to m, the intensity recorded at time j.

For each time j, the set of n measures $\{S(i,j), i=1 \text{ to } n\}$ the following may be defined as discussed above:

$Max(j) = \text{Maximum}(\{S(i,j), i=1 \text{ to } n\})$ (the third series)

$Min(j) = \text{Minimum}(\{S(i,j), i=1 \text{ to } n\})$ (the second series)

$Mean(j) = \text{Mean}\{S(i,j), i=1 \text{ to } n\})$ (the fourth series)

To have a flexible model, new limits may be defined with scaling factors alpha and beta:

MaxNew(j)=Alpha*Maximum({S(i,j),i=1 to n}),Alpha≥1

MinNew(j)=Beta*Minimum({S(i,j),i=1 to n}), 0<beta≤1

Alpha and Beta may be defined on the basis of the typical degree of variation between allowable samples for the product category in question, as determined during a learning phase for example as discussed with reference to FIG. 7.

Meanwhile, the first series comprises M(j), j=1 to m, the set of measurements generated when an unknown sample is analyzed. For each j, the value M(j) may considered as an outlier if:

M(j)>MaxNew(j) or M(j)<MinNew(j)

Figure 6:
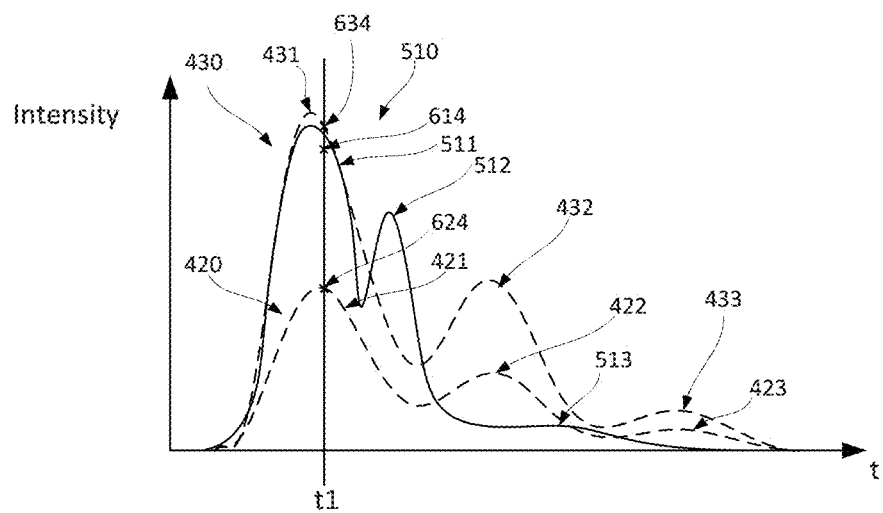
FIG. 6 shows a representation of an exemplary second and third series of values in accordance with the embodiment of FIG. 2 in comparison with the first series of measurements.

FIG. 6 shows a representation of an exemplary second and third series of values in accordance with the embodiment of FIG. 2 in comparison with the first series of measurements.

As shown, by way of example a particular measurement 614 in the first series corresponding to the time t1 in the measurement process is compared with a corresponding (i.e. defined for the same time interval t1) minimum value 624 in the second series defined for the specified category.

This comparison is carried out for each value in the first series.

The method then proceeds to step 215 at which each measurement in the first series is compared with a corresponding maximum value in a third series defined for the specified category.

As shown, by way of example a particular measurement 614 in the first series corresponding to the time t1 in the measurement process is compared with a corresponding (i.e. defined for the same time interval t1) maximum value 634 in the third series defined for the specified category.

This comparison is carried out for each value in the first series.

It will be appreciated that although described sequentially, steps 210 and 215 may be carried out in parallel for each value in the first series.

Still further, it will be appreciated that while the preceding description proceeds on the basis that all measurements of the first series are received before then being compared en-bloc with the values of the second and third series, these steps may be carried out on a per-measurement basis, such that each new measurement is compared to corresponding values in the second and third series as it is received, and before the complete first series is available.

The first and second series may be stored as separate respective values, or otherwise. For example, they may be stored as a single reference value in a fourth series, together with a deviation value indicating the difference between each value in the second or third series and the corresponding value in the fourth series.

FIG. 7 shows a representation of an exemplary second and third series of values in accordance with the embodiment of FIG. 2 defined with reference to a fourth series.

FIG. 7 follows the same layout as FIG. 1 as described above, with intensity plotted on the vertical axis and time on the horizontal axis. The fourth series of values 740 is plotted similarly to the curves 420 and 430, representing an instantaneous average between all generated learning values, such that peak 741 aligns with the peaks 431 and 421, the peak 742 aligns with the peaks 432 and 422 and the peak 743 aligns with the peaks 433 and 423.

In certain embodiments, the fourth series may be obtained through a learning process, whereby one or more sets of measurements are performed for one or more samples known to be representative of a particular analyte. For example, in embodiments where the characterizing to be performed constitutes a determination that the analyte meets, or does not meet, certain quality criteria, the fourth series may be obtained by performing one or more sets of measurements for one or more samples known to be representative of that analyte. The fourth series may then represent the average values across the sets of measurements where more than one set of measurements of the representative analyte are performed, and the second and third series may represent the respective maximum and minimum values encountered across those sets of measurements. Where this approach is followed, the respective maximum and minimum values may be multiplied by and additional margin of tolerance (maximum values being increased by a predetermined proportion alpha, and minimum values being decreased by a predetermined proportion beta as introduced above). The margin of tolerance may be a proportion of the absolute value, or a proportion of the instantaneous deviation from the mean. The proportion may be fixed, or may vary on the basis of the nature of the sample (for a given category of products, certain variations may be more acceptable than others), on the type of sensor used (certain sensors may be more or less sensitive to different components, and thus more likely to produce anomalous values in certain regions of their measurement series), or on the basis of statistical characteristics of the measurement sets (for example, in regions where a greater variation between samples is observed, it may be desirable to expand the tolerance margin). In other embodiments, in particular where only one representative measurement set is obtained, the second and third series may be set directly as predefined proportions of the fourth series (corresponding the measurement set itself).

Regardless of the manner in which the second and third series are defined or stored, the method next proceeds to step 220, at which any adjacent measurements exceeding the corresponding maximum values or where any adjacent measurements falling below the corresponding minimum value are grouped.

On this basis, values may be noted as "Out" for the indexes set of all the outlier points:

$$Out = \{j, \text{ where } M(j) > MaxNew(j) \text{ or } M(j) < MinNew(j)\}$$

Optionally, a dissimilarity index may be defined, for example by $$Diss(j) = \begin{cases} 100 * \left(10 \frac{MaxNew(j)}{M(j)}\right) & \text{if } M(j) > MaxNew(j) \\ 0 & \text{if } MinNew(j) \leq M(j) \text{ and } M(j) \leq MaxNew(j) \\ 100 * \left(10 \frac{M(j)}{MinNew(j)}\right) & \text{if } M(j) < MinNew(j) \end{cases}$$

One can see that this dissimilarity index is greater than 0 and smaller than 100. For each outlier, more the value M(j) is different of MinNew(j) or MaxNew(j) more the dissimilarity value is near 100.

Accordingly, there may be provided an additional step such that where any measurement exceeds the corresponding maximum value a dissimilarity index is calculated for that respective measurement exceeding the corresponding maximum value, this dissimilarity index reflecting the degree by which the corresponding maximum value is exceeded, and where any measurement falls below the corresponding minimum value the dissimilarity index is calculated for that respective measurement falling below the corresponding minimum value, the dissimilarity index reflecting the degree by which the measurement falls below the corresponding minimum value.

More particularly, the grouping process may be implemented as follows:

Step 0: measurements corresponding to the "Out" criteria are sorted in ascending order.

Step i: Identify index "k" so that "Out(k+1)−Out(k)> Sigma", where Sigma is a "parameter number" which may be defined by the user. The $i^{th}$ group is defined by:

Group($i$)={Out($h$),$h$ to $k$}

We extract Group(i) from "Out". If the new "Out" is not empty, we go to the next step "Step (i+1)".

At the end, we have a partition of p groups.

P1=Group($i$),$i$=1 to $p$

Figure 8:
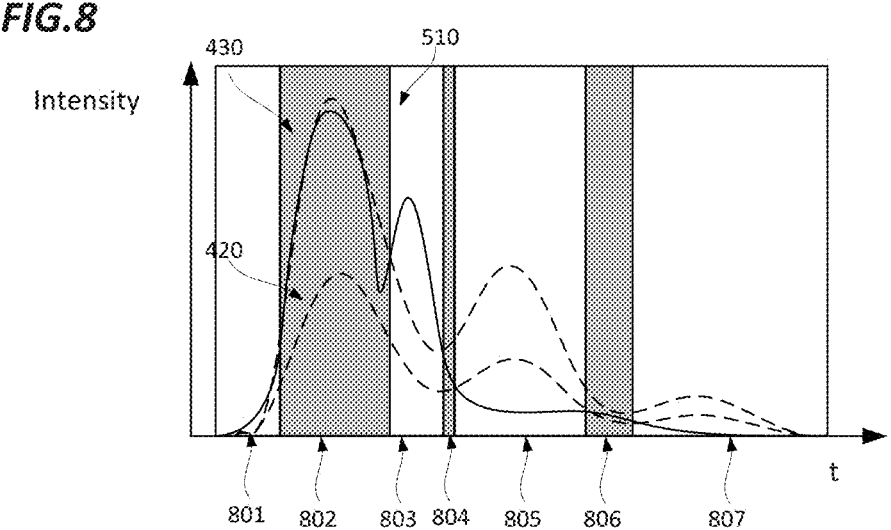
FIG. 8 shows a representation of a grouping based on the exemplary second and third series of values of FIG. 6.

FIG. 8 shows a representation of a grouping based on the exemplary second and third series of values of FIG. 6.

As shown, the curves 510, 420, 430 of FIG. 8 are divided on the horizontal axis into seven sections. Sections 802, 804 and 806 correspond to sets of adjacent measurements falling between the maximum values defined by curve 430 and the minimum values defined by curve 420. Sections 801 and 803 correspond to sets of adjacent measurements exceeding the maximum values defined by the third series 430. Sections 805 and 807 correspond to sets of adjacent measurements falling below the minimum values defined by the second series 430. As such, the adjacent measurements in sections 801, 803, 805 and 807 are grouped into respective groups at step 220.

Finally at step 225 the groups identified at step 220 as falling outside the maximum or minimum values are flagged as anomalous. This flagging may involve the explicit addition of metadata to the measurement values, or be implicit in the grouping that is carried out, for example where this leads to the grouped values being stored separately.

By flagging the anomalous values in this manner provides the basis for a characterization—any analyte having an anomalous group, or a predetermined number of anomalous groups might be characterized as not meeting quality criteria.

The optional calculation of dissimilarity values provides further basis for a characterization—any analyte demonstrates an overall dissimilarity above a predetermined threshold might be characterised as not meeting quality criteria.

In certain embodiments, the method may proceed beyond the flagging of anomalous groups, and attempt to determine their origin. In certain embodiments, this may involve comparing the measurements in each group to a set of reference datasets, and identifying the reference data set corresponding most closely to the measurements in the group. These reference data sets, or libraries, may comprise sets of data like those described with respect to FIG. 1 or 7 for example, but corresponding to categories other than the selected category defined for the series of measurements. The categories represented in these reference datasets might be general, permitting the identification of any arbitrary foreign component, or may be predefined to correspond to common or known foreign components for the selected category. For example, if the selected category is "coffees" the additional reference datasets retained for the identification of foreign components might comprise other agricultural products, other food stuffs, and parasites known to affect coffees.

In accordance with certain embodiments, there may be provided a further step of classifying each group identified at step 220 into a respective classification selected from a predefined set of classifications, where each classification describes the form of the measurements comprising the respective group and the form of the corresponding values of the second series, the third series, or the fourth series. For example, the form may be a rising area, a falling area, a flat area, a peak, a trough or the like. As such, in a case where an additional reference dataset is found, the analyte may be further characterized by incorporating characteristics of the corresponding reference data set.

Specifically, according to certain embodiments one or more categories may be defined corresponding to a situation where:

a group defines an extremum and the corresponding values in the second series, the third series, or the fourth series also define an extremum; or a group does not define an extremum and the corresponding values in the second series, the third series, or the fourth series do define an extremum; or a group defines an extremum and the corresponding values in the second series, the third series, or the fourth series do not define an extremum; or neither the group nor the corresponding values in the second series, the third series, or the fourth series define an extremum, and the values of the measurements in that group exceed the corresponding values in the third series; or neither the group nor the corresponding values in the second series, the third series, or the fourth series define an extremum, and the values of the measurements in a respective group fall below the corresponding values in the second series.

This may be achieved on the basis of the method described in European patent application EP1845479.

Peaks of the second, third or fourth series representing the reference data set (Target) may be considered on one hand, and the first series, representing the analyte (Unknown) on the other, and classified according to Group($i$) Type is $$\begin{cases} 1 \text{ if it contains a Peak of Target and a Peak of Unknown} \\ 2 \text{ if it contains a Peak of Target But Not a Peak of Unknown} \\ 3 \text{ if it dont contains a Peak of Target but a Peak of Unknown} \\ 4 \text{ if no peaks Present but the intensities} \geq \text{than } MaxNew \\ 5 \text{ if no peaks Present but the intensities} \leq \text{than } MinNew \end{cases}$$

On this basis, group 801 would fall in category 4, group 803 would fall in category 2, group 805 would fall in category 1, and group 807 would fall in category 3.

On this basis a new partition of five classes corresponding to the above defined group types, P={P(1), P(2), P(3), P(4), P(5)} can be determined covering all the outliers. For each j, j=1 to 5, class "P(j)" contains all the groups of type j.

Each of them, represent certain difference between the unknown sample and the target. The dissimilarity value discussed above may be used to quantify this difference.

For each class "P (j)", j=1 to 5, one associates a class "PDiss (j)", that contains all the dissimilarity values of all "P (j)" elements.

The applicability of the five group types presented above depends to some extent on the typical curve produced by the sensor providing the measurements. While the five group types presented above work well for the curve produced by a Gas Chromatograph for example, they may be less applicable for curves produced by a MOS sensor for example, since MOS sensors may not produce a series of discrete peaks, but rather a complex continuous form. Where this is the case, a subset of the five group types presented above may be used. For example, where a particular sensor does not produce discrete peaks, group types 1, 2 and 3 may be omitted. Furthermore, in some embodiments the set of group types may be expanded with further group types, relating for example to the rate of change of the curve.

Each "PDiss (j)" set may then be sorted by ascending order. A value "Criter(j)", equal to a mean of "parameter portion", for example the last 10%, of the last high elements of "PDiss (j)" may be noted The analyte will be considered different from the target according to class "P (j)" if "Criter(j)" is greater than a "parameter threshold" selected by the user.

A global final criterion for comparison of the analyte to the reference dataset. To do this, all "PDiss (j)" may be regrouped in a classes in a set "Diss". After sorting the last by ascending order, a mean of "parameter portion" (For example the last 10%) of the last high elements of "Diss" is calculated.

The Analyte may be considered globally different from the reference dataset if "Criter" is greater than a predetermined threshold.

The optional categorisation of groups provides further basis for a characterization, for example, certain categories may be considered to be more indicative of a quality issue than others. For example, the presence of a peak in the first series, but none in the fourth may indicate a contaminant, which may be a greater concern than a peak occurring as expected, but being larger or smaller than anticipated.

These considerations are further improved when combined with the dissimilarity calculations presented above—by calculating dissimilarity per group, different dissimilarity thresholds may be set depending on the group type, reflecting the relative significance of each group type.

Characterization may go beyond determining whether or not the analyte meets quality criteria, and include the identification of the cause of any detected anomalies.

The form of the set of values in a group will generally be suggestive of the root of the cause for the deviation between the model values defined by the second, third or fourth series and the measured values. For example, an extra peak will generally suggest the presence of a contaminant, whilst an unexpected trough may suggest a variation in quality or the absence of a component. Thus, the steps of comparing the measurements in each group to a set of reference datasets, and identifying the reference data set corresponding most closely to the measurements may then be performed with regard to these classifications.

Further characterization may be performed by comparison of anomalous groups with additional reference data sets.

Figure 9:
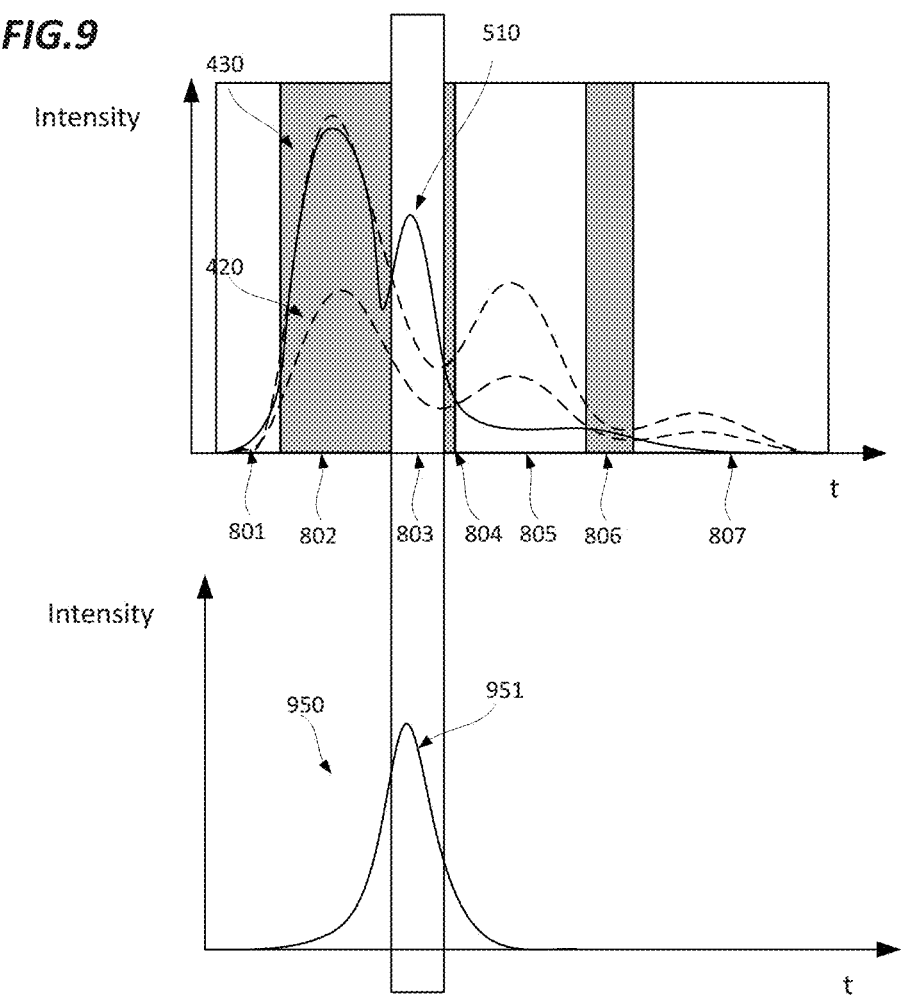
FIG. 9 shows a representation of the comparison of anomalous grouping with a reference dataset.

FIG. 9 shows a representation of the comparison of anomalous grouping with a reference dataset.

As shown, FIG. 9 presents two sets of axes. The first is identical to that of FIG. 8, and in particular shows the anomalous groups 801, 803, 805 and 807. In accordance with certain embodiments, a set of reference datasets is compared to each of these anomalous groups with a view to identifying features in those additional reference datasets having features corresponding to one or more of the anomalous groups.

The second set of axes follows the same layout as the first with Intensity plotted on the vertical axis and time on the horizontal axis. A fifth series of values 950 corresponding to an additional reference dataset is plotted similarly to the curves 420 and 430. While this reference dataset 950 may be one of many considered, it may be noted that the curve 950 corresponds to the group 803, which constitutes a number of anomalously high adjacent values in the measured values of the first series. Combining the mean curve 741 for the selected category and this curve 950 would provide a closely matching set of values for the measurements in group 803, so that in accordance with certain embodiments the results of the measurement may be annotated as possibly contaminated with whatever substance the curve 950 corresponds to.

According to certain embodiments there is provided a method or apparatus for characterizing a product sample for example in comparison to a reference sample using a sensor such as a gas chromatograph or a MOS sensor. This characterization may comprise an indication of whether or not the product sample conforms to a quality criterion. The comparison of the sensor output measurements for the product sample is compared to maximum and minimum value curves, which may be derived from measurements of the reference sample, whereby adjacent samples outside the envelope defined by these maximum and minimum values are grouped together. A dissimilarity index may be determined for the anomalous values as a whole, or on a per group basis. The groups may be classified depending on the shape they describe, in particular the presence, or not, of peaks, and correspondingly the shape of the corresponding part of the envelope. These determinations may then be used as the basis of the conformity indication, and also the basis for attempting to identify the cause of any anomalies, in particular the identification of foreign components.

The disclosed methods can take form of an entirely hardware embodiment (e.g. FPGA), an entirely software embodiment (for example to control a system according to the invention) or an embodiment containing both hardware and software elements. Software embodiments include but are not limited to firmware, resident software, microcode, etc. The invention can take the form of a computer program product accessible from a computer-usable or computer-readable medium providing program code for use by or in connection with a computer or an instruction execution system. A computer-usable or computer-readable can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

In particular, there is provided an apparatus for characterizing an analyte of a specified category, the apparatus being adapted to:

receive a first series of measurements of a physical parameter from a sensor, the measurements varying monotonically within a range of values, compare each measurement in the first series with a corresponding minimum value in a second series defined for the specified category and a corresponding maximum value in a third series defined for the specified category, group any adjacent the measurements where each measurement in the group exceeds the corresponding maximum value or where each measurement in the group each falls below the corresponding minimum value, and to flag the groups as anomalous.

These methods and processes may be implemented by means of computer-application programs or services, an application-programming interface (API), a library, and/or other computer-program product, or any combination of such entities.

Figure 10:
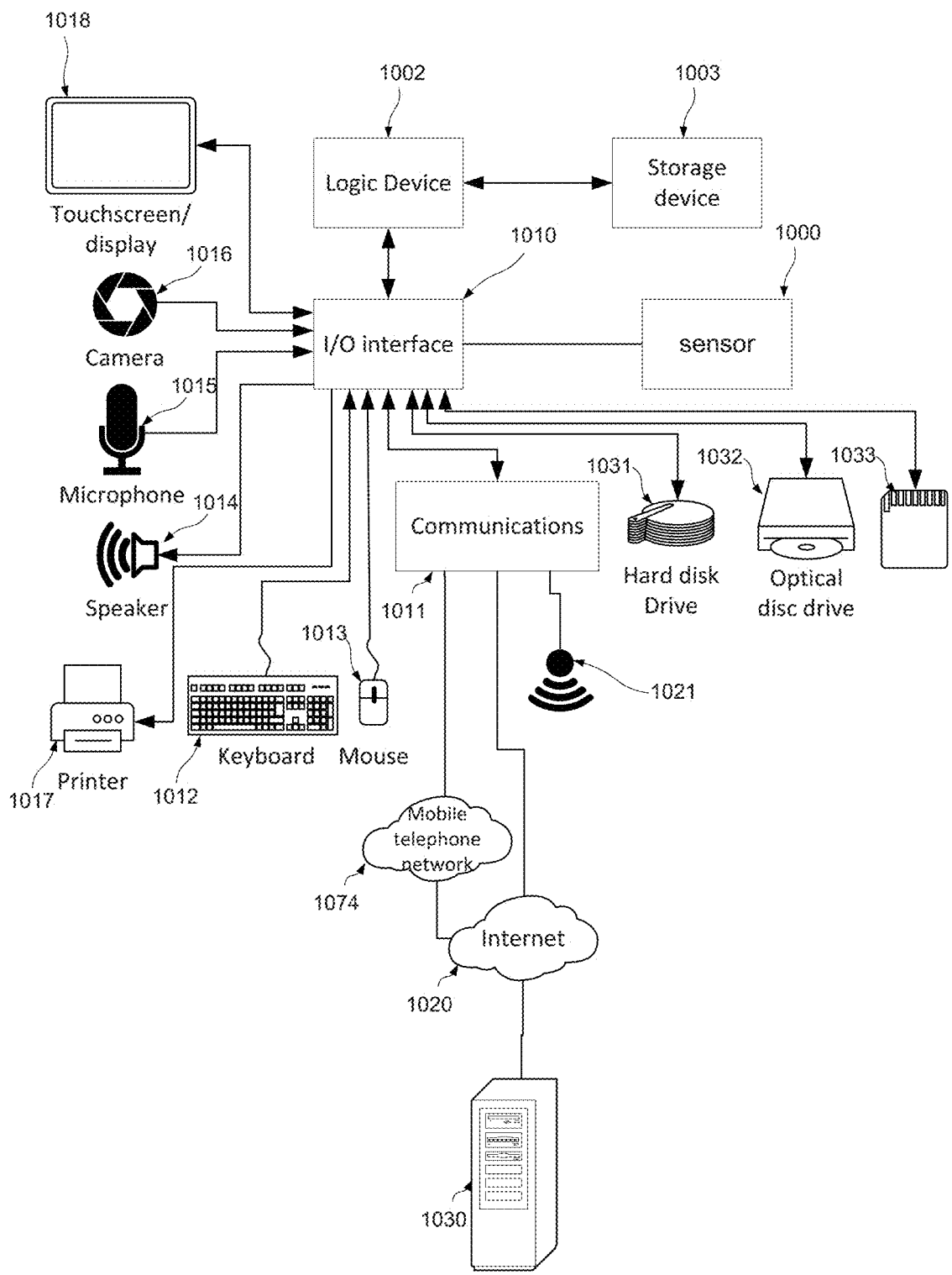
FIG. 10 shows a generic computing system adaptable for implementation of embodiments of the invention.

FIG. 10 shows a generic computing system adaptable for implementation of embodiments of the invention.

A shown in FIG. 10, a system includes a logic device 1002 and a storage device 1003. The system may optionally include a display subsystem 1018, input/output subsystem 1010, communication subsystem 1011, and/or other components not shown.

Logic device 1002 includes one or more physical devices configured to execute instructions. For example, the logic device 1002 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 1002 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device 1002 optionally may be distributed among two or more separate devices, which may be remotely located and/or configured for coordinated processing. Aspects of the logic device 1002 may be virtualized and executed by remotely accessible, networked computing devices configured in a cloud-computing configuration.

Storage device 1003 includes one or more physical devices configured to hold instructions executable by the logic device to implement the methods and processes described herein. When such methods and processes are implemented, the state of storage device 1003 may be transformed—e.g., to hold different data.

Storage device 1003 may include removable and/or built-in devices. Storage device 1003 may comprise one or more types of storage device including optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage device may include volatile, non-volatile, dynamic, static, read/write, read-only, random-access, sequential-access, location-addressable, file-addressable, and/or content-addressable devices.

In certain arrangements, the system may comprise an interface 1010 adapted to support communications between the Logic device 1002 and further system components, in particular the sensor 1000, which as described above provides the first series of measurements of the analyte.

For example, additional system components may comprise removable and/or built-in extended storage devices. Extended storage devices may comprise one or more types of storage device including optical memory 1032 (e.g., CD, DVD, HD-DVD, Blu-Ray Disc, etc.), semiconductor memory 1033 (e.g., RAM, EPROM, EEPROM, FLASH etc.), and/or magnetic memory 1031 (e.g., hard-disk drive, floppy-disk drive, tape drive, MRAM, etc.), among others. Such extended storage device may include volatile, non-volatile, dynamic, static, read/write, read-only, random-access, sequential-access, location-addressable, file-addressable, and/or content-addressable devices.

It will be appreciated that storage device includes one or more physical devices, and excludes propagating signals per se. However, aspects of the instructions described herein alternatively may be propagated by a communication medium (e.g., an electromagnetic signal, an optical signal, etc.), as opposed to being stored on a storage device.

Aspects of logic device 1002 and storage device 1003 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system implemented to perform a particular function. In some cases, a program may be instantiated via logic device executing machine-readable instructions held by storage device. It will be understood that different modules may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

Figure 11:
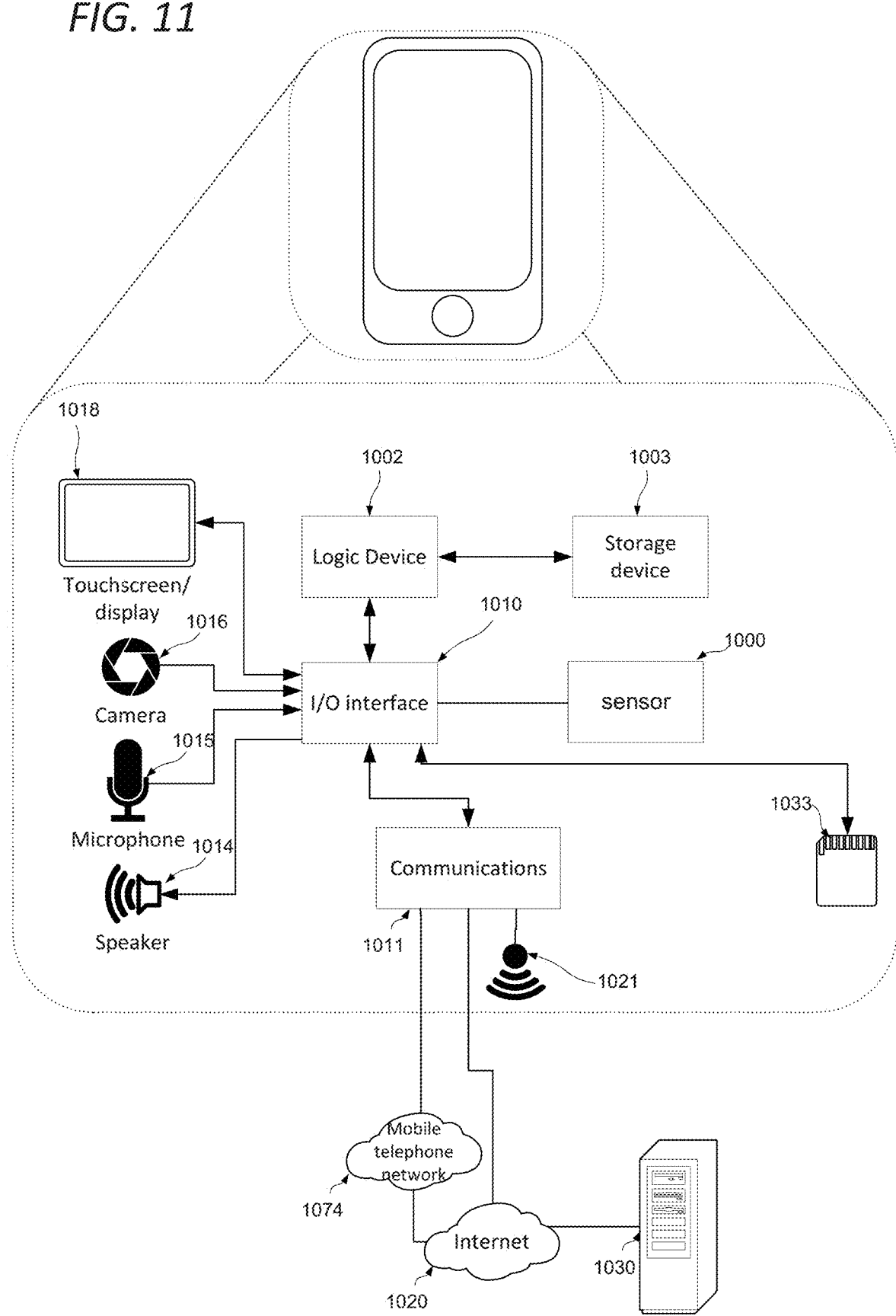
FIG. 11 shows a smartphone device adaptable to constitute an embodiment.

In particular, the system of FIG. 11 may be used to implement embodiments of the invention.

For example a program such as one implementing the steps described with respect to FIG. 2 may be stored in storage device 1003 and executed by logic device 1002. Furthermore, a program such as one implementing the generation of a characterisation library as described above may be stored in storage device 1003 and executed by logic device 1002. The communications interface 1011 may receive the second, third or fourth series, reference datasets and the like from the server 1030, and upload sample type information or sample characterization data as discussed above. The Logic device 1002 may receive and compile the first series analyte measurements, perform any additional processing, compare the first series analyte measurements with the second, third or fourth series, reference datasets and the like, and report the results to the user via display 1018. At various stages of the operation further inputs, for example concerning the sample type, may be prompted via the display 1018, and recovered via the user input interface devices 1016, 1015, 1014, 1013, 1012 as described below under the control of a suitable program, or may interface with internal or external dedicated systems adapted to perform some or all of these processes.

Accordingly the invention may be embodied in the form of a computer program.

It will be appreciated that a "service", as used herein, is an application program executable across multiple user sessions. A service may be available to one or more system components, programs, and/or other services. In some implementations, a service may run on one or more server-computing devices.

When included, display subsystem 1018 may be used to present a visual representation of data held by storage device, in particular a representation of the first, second, third or fourth series, reference datasets and the like, or any combination of these. This visual representation may take the form of a graphical user interface (GUI). As the herein described methods and processes change the data held by the storage device 1003, and thus transform the state of the storage device 1003, the state of display subsystem 1018 may likewise be transformed to visually represent changes in the underlying data. Display subsystem 1018 may include one or more display devices utilizing virtually any type of technology. Such display devices may be combined with logic device and/or storage device in a shared enclosure, or such display devices may be peripheral display devices.

When included, input/output subsystem 1010 may comprise or interface with one or more user-input devices such as a keyboard 1012, mouse 1013, speaker 1014, Microphone 1015, camera 1016, printer 1017, display or touch screen 1018, near field communications interface 1021, or game controller (not shown). In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, colour, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1011 may be configured to communicatively couple computing system with one or more other computing devices. For example, communication module of may communicatively couple computing device to remote service hosted for example on a remote server 1030 via a network of any size including for example a personal area network, local area network, wide area network, or the internet. Communication subsystem may include wired and/or wireless communication devices compatible with one or more different communication protocols. As non-limiting examples, the communication subsystem may be configured for communication via a wireless telephone network 1074, or a wired or wireless local- or wide-area network. In some embodiments, the communication subsystem may allow computing system to send and/or receive messages to and/or from other devices via a network such as the Internet 1020. The communications subsystem may additionally support short range inductive communications 1021 with passive devices (NFC, RFID etc).

Figure 12:
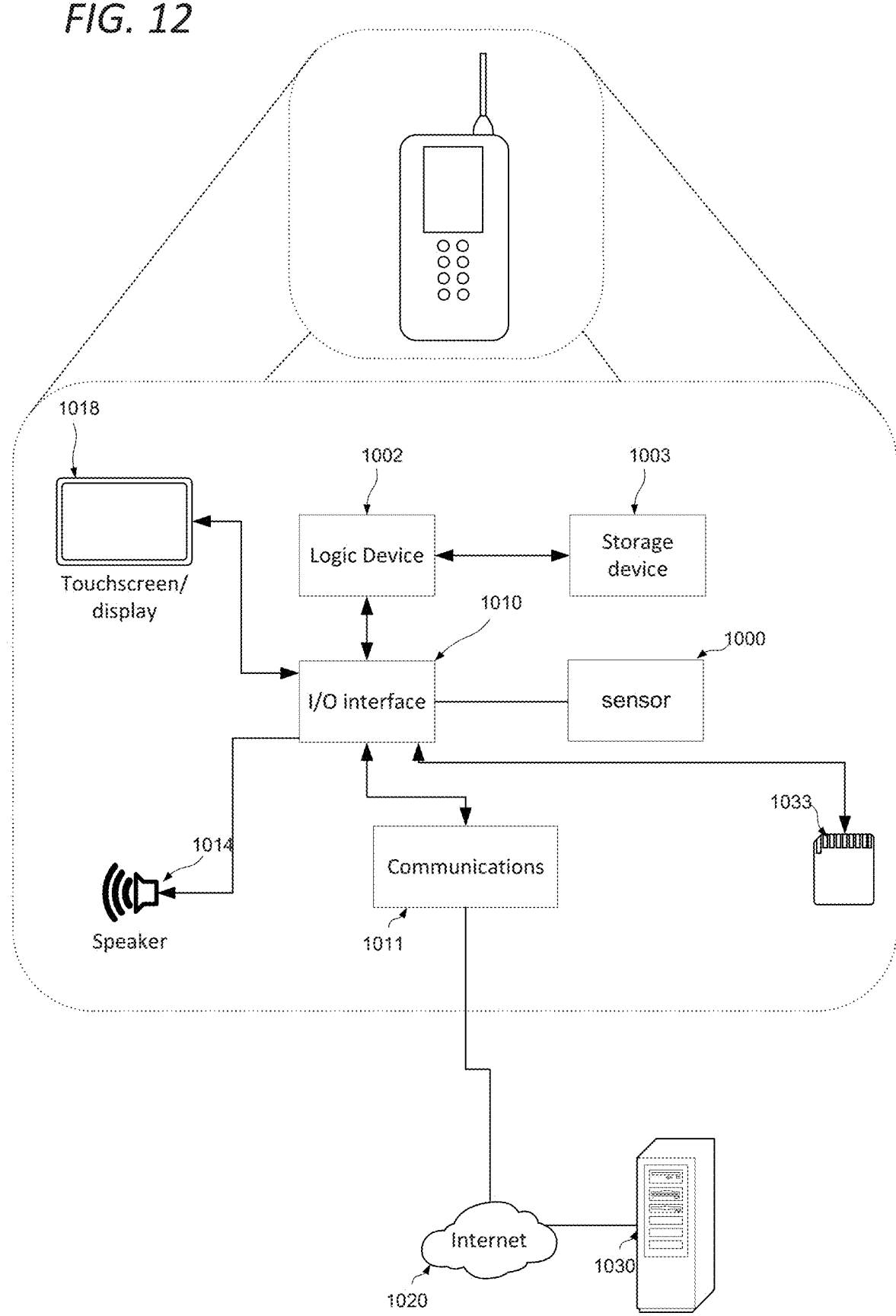
FIG. 12 shows a hand scanner device adaptable to constitute an embodiment.
Figure 13:
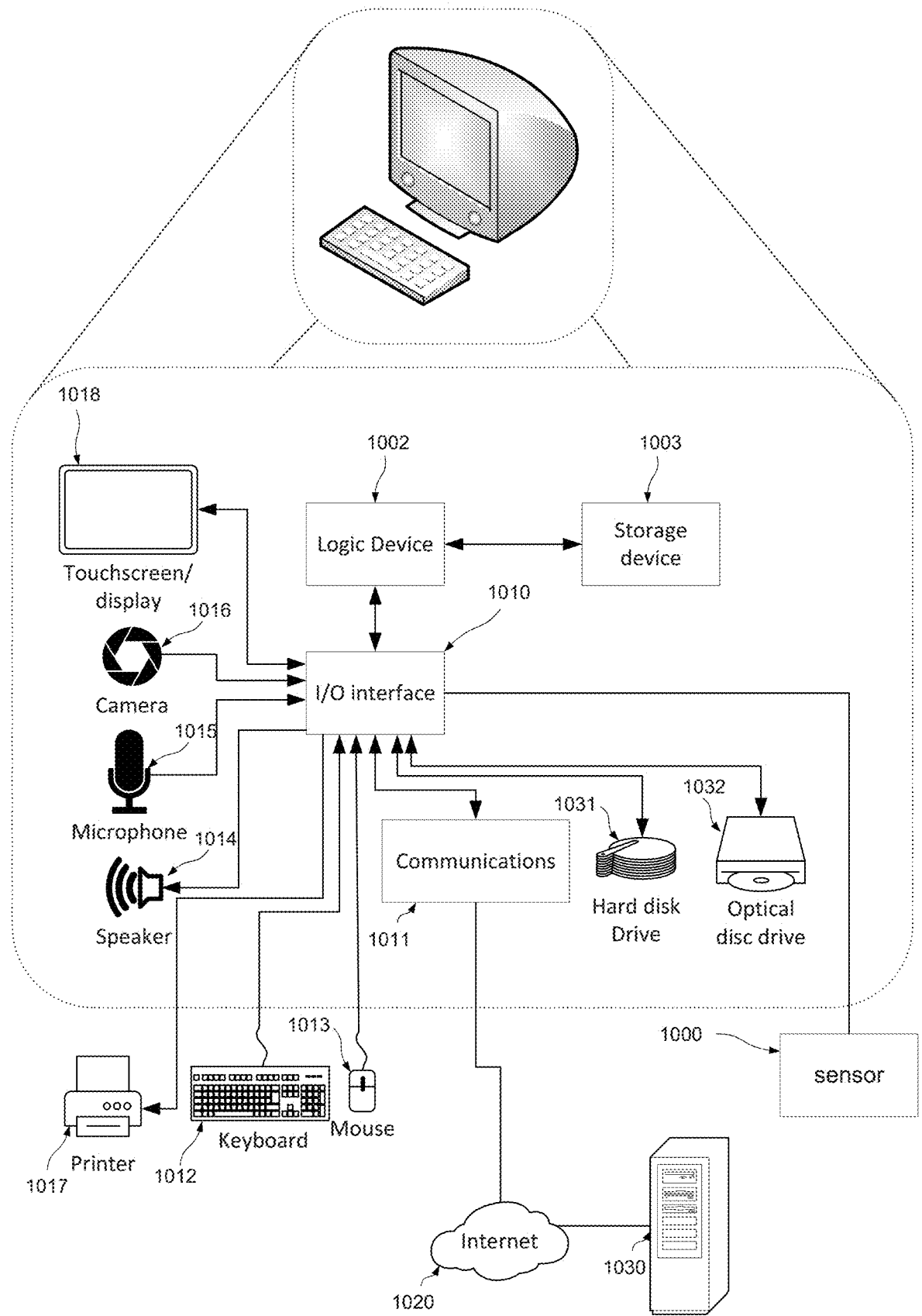
FIG. 13 shows a desktop computer device adaptable to constitute an embodiment.

The system of FIG. 10 is intended to reflect a broad range of different types of information handling system. It will be appreciated that many of the subsystems and features described with respect to FIG. 10 are not required for implementation of the invention, but are included to more realistically reflect common systems. It will be appreciated that system architectures vary widely, and the relationship between the different sub-systems of FIG. 10 is merely schematic, and is likely to vary in terms of layout and the distribution of roles in real systems. It will be appreciated that in practice, systems are likely to incorporate different subsets of the various features and subsystems described with respect to FIG. 10. FIGS. 11, 12 and 13 discuss in further detail some common example devices.

FIG. 11 shows a smartphone device adaptable to constitute an embodiment. As shown in FIG. 11, the smartphone device incorporates elements 1002, 1003, 1011, 1000, 1016, 1015, 1014, 1018, 1011, 1021 and 1033 as described above. It is in communication with the telephone network 1074 and a server 1030 via the network 1020.

FIG. 12 shows a hand scanner device adaptable to constitute an embodiment. As shown in FIG. 12, the hand scanner device incorporates elements 1002, 1003, 1010, 1000, 1018, 1011, 1014, 1033, 1020 and 1030 as described above. It is in communication with a server 1030 via the network 1020.

FIG. 13 shows a desktop computer device adaptable to constitute an embodiment. As shown in FIG. 13, the desktop computer device incorporates elements 1002, 1003, 1010, 1018, 1011, 1017, 1016, 1015, 1014, 1013, 1012, 1031 and 1032 as described above. It is in communication with elements 1017, 1012, 1013 and 1000 as peripheral devices, and with a server 1030 via the network 1020.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The examples described above are given as illustrations of embodiments of the invention. They do not in any way limit the scope of the invention which is defined by the following claims.

The invention claimed is:

1. A method for characterizing an analyte of a specified category, said method comprising:
   receiving a first series of measurements of a physical parameter from a sensor;
   comparing each said measurement in said first series with a corresponding minimum value in a second series defined for said specified category and a corresponding maximum value in a third series defined for said specified category,
   grouping any adjacent said measurements where each said measurement in said group exceeds said corresponding maximum value or where each said measurement in said group each falls below said corresponding minimum value;
   flagging each said group as anomalous; and
   classifying each said group into a respective classification selected from a predefined set of classifications, where each said classification in said predefined set of classifications describes the form of the measurements comprising said respective group and the form of the corresponding values of said second series, said third series, or a fourth series representing the average values across the sets of measurements where more than one set of measurements of the representative analyte are performed.

2. The method of claim 1 wherein said characterization comprises an indication of whether said analyte meets a quality criterion, and wherein said method further comprising determining whether said groups reflect a departure from said quality criterion.

3. The method of claim 1 further comprising defining said second series and said third series on the basis of one or more sets of measurements performed for one or more samples known to be representative of a particular analyte.

4. The method of claim 1 further comprising advancing or delaying said first series with respect to said second and third series so as to obtain the best possible alignment.

5. The method of claim 4 further comprising if any said measurement exceeds said corresponding maximum value, calculating a dissimilarity index for that respective measurement exceeding said corresponding maximum value, said dissimilarity index reflecting the degree by which said corresponding maximum value is exceeded, and where any said measurement falls below said corresponding minimum value said dissimilarity index is calculated for that respective measurement falling below said corresponding minimum value, said dissimilarity index reflecting the degree by which said measurement falls below said corresponding minimum value.

6. The method of claim 1 wherein at least one of said classifications corresponds to a situation where:
 a respective said group defines an extremum and the corresponding values in said second series, said third series, or said fourth series also define an extremum; or
 a respective said group defines an extremum and the corresponding values in said second series, said third series, or said fourth series do not define an extremum; or
 a respective said group does not define an extremum and the corresponding values in said second series, said third series, or said fourth series do define an extremum; or
 neither a respective said group nor the corresponding values in said second series, said third series, or said fourth series define an extremum, and the values of the measurements in a respective said group exceed the corresponding values in said second series; or
 neither a respective said group nor the corresponding values in said second series, said third series, or said fourth series define an extremum, and the values of the measurements in a respective said group fall below the corresponding values in said third series.

7. The method of claim 1 further comprising:
 comparing the measurements in one or more said groups to a set of additional reference datasets;
 identifying the reference data set in said set of additional reference sets corresponding most closely to said measurements in said group; and
 associating said analyte with characteristics of said corresponding reference data set.

8. The method of claim 7 wherein said comparing the measurements in each said group to a set of additional reference datasets, and said identifying the reference data set corresponding most closely to said measurements are performed with regard to said classifications.

9. The method of claim 8 wherein said sensor is any sensor producing a value evolving over time when exposed to an analyte, and wherein said first series of measurements varying monotonically within a range of values, corresponds to a series of measurements obtained over a measurement period.

10. The method of claim 9 wherein said sensor is a MOS sensor or a Gas Chromatograph.

11. An apparatus for characterizing an analyte of a specified category, said apparatus adapted to:
 receive a first series of measurements of a physical parameter from a sensor;
 compare each said measurement in said first series with a corresponding minimum value in a second series defined for said specified category and a corresponding maximum value in a third series defined for said specified category, group any adjacent said measurements where each said measurement in said group exceeds said corresponding maximum value or where each said measurement in said group each falls below said corresponding minimum value;
 flag said groups as anomalous; and
 classify each said group into a respective classification selected from a predefined set of classifications, where each said classification in said predefined set of classifications describes the form of the measurements comprising said respective group and the form of the corresponding values of said second series, said third series, or a fourth series representing the average values across the sets of measurements where more than one set of measurements of the representative analyte are performed.

12. An apparatus adapted to implement the method of claim 4.

13. A computer program product having computer code stored in a non-transitory computer storage medium wherein the computer code when executed by at least one processor is adapted to implement the method of claim 1.

* * * * *